United States Patent [19]

Babb et al.

[11] Patent Number: 4,671,298
[45] Date of Patent: Jun. 9, 1987

[54] ISOTHERMAL REBREATHING APPARATUS AND METHOD

[75] Inventors: Albert L. Babb; Michael P. Hlastala, both of Seattle, Wash.

[73] Assignee: Meridian Medical Corporation, Bellevue, Wash.

[21] Appl. No.: 674,941

[22] Filed: Nov. 26, 1984

[51] Int. Cl.$^4$ .............................................. A61B 5/00
[52] U.S. Cl. .................................... 128/719; 128/125; 128/727; 128/200.13; 128/204.17; 422/84; 422/108; 422/109; 436/132; 436/900
[58] Field of Search ................. 436/132, 900; 422/84, 422/108, 109; 128/718, 719, 630, 725, 727, 728, 201.13, 204.17

[56] References Cited

U.S. PATENT DOCUMENTS

| | | | |
|---|---|---|---|
| 3,522,009 | 7/1970 | Borkenstein | 422/85 |
| 3,527,205 | 9/1970 | William Jones | 128/728 |
| 3,552,930 | 1/1971 | Borkenstein | 422/85 |
| 3,622,278 | 11/1971 | Elzinga | 436/900 |
| 3,676,073 | 7/1972 | Luckey | 436/132 |
| 3,714,942 | 2/1973 | Fischet et al. | 128/204.17 |
| 3,764,270 | 10/1973 | Collier et al. | 128/719 |
| 3,948,604 | 4/1976 | Hoppesch | 436/132 |
| 4,196,728 | 4/1980 | Granite | 128/204.17 |
| 4,277,251 | 7/1981 | Leichnitz | 422/85 |
| 4,278,636 | 7/1981 | Voigt et al. | 422/84 |
| 4,314,564 | 2/1982 | Albarda | 129/719 |
| 4,316,380 | 2/1982 | Heim et al. | 128/719 |
| 4,459,994 | 7/1984 | Slemeyer | 128/719 |

FOREIGN PATENT DOCUMENTS

| | | | |
|---|---|---|---|
| 2818605 | 11/1978 | Fed. Rep. of Germany | 128/719 |
| 1168529 | 10/1969 | United Kingdom | 422/85 |

OTHER PUBLICATIONS

Wright, et al.: Breath Alcohol Analysis and the Blood: Breath Ratio Medicine Science Law 15(3): 205-210, 1975.
A. W. Jones: Determination of Liquid/Air Partition Coefficients for Dilute Solutions of Ethanol in Water, Whole Blood, and Plasma, Journal of Analytical Toxicology 7:193-197, 1983.
Mason and Dubowski: Breath Alcohol Analysis: Uses, Methods, and Some Forensic Problems-Review and Opinion, Journal of Forensic Science, 33:9-41, 1976.
A. W. Jones: How Breathing Technique Can Influence the Results of Breath-Alcohol Analysis, Medical Science Law, 4:275-280, 1982.
Harger et al.: Estimation of the Level of Blood Alcohol from Analysis of Breath II. Use of Rebreathed Air, Journal of Studies in Alcohol, 17:1-18, 1956.
A. W. Jones: Effects of Temperature and Humidity of Inhaled Air on the Concentration of Ethanol in a Man's Exhaled Breath, Clinical Science, 63:441-445, 1982.
A. W. Jones: Role of Rebreathing in Determination of the Blood Breath Ratio of Exhaled Ethanol, JAP: Respir Environ Exercise Physiol 55:1237-1241, 1983.
Russell and Jones: Breath Ethyl Alcohol Concentration and Analysis in the Presence of Chronic Obstructive Pulmonary Disease, Clinical Biochemistry 16:182-187, 1983.

(List continued on next page.)

*Primary Examiner*—S. Leon Bashore
*Assistant Examiner*—V. Manoharan
*Attorney, Agent, or Firm*—Hughes & Cassidy

[57] ABSTRACT

A isothermal rebreathing apparatus and method for collecting human breath samples for chemical analysis of the ethyl alcohol content wherein the breath samples are obtained from a subject repetitively exhaling into the inhaling from an enclosed, flexible, variable volume, bag-like collection receptacle which is heated to maintain the breath sample enclosed therein at a prescribed temperature, preferably at or near the subject's body temperature, before extracting the breath sample for subsequent chemical analysis. The collection receptacle may be enclosed by an airtight chamber including heaters therein to warm the air around the collection receptacle in order to regulate the temperature of the breath sample therein. A bellows section in fluid communication with the heating chamber allows for inflation and deflation of the flexible collection receptacle while located in an airtight environment.

21 Claims, 7 Drawing Figures

OTHER PUBLICATIONS

Schwartz, et al.: Ein nueues Verfahren zur Bestimmung des Blutalkoholgehaltes uber die Atemluft bei Bewusstlosen, Anaesthetist 31:177-180, 1982.

A. Slemeyer: Analytical Model Describing the Exchange Processes of Alcohol in the Respiratory System, Alcohol, Drugs and Traffic Safety, ed. by L. Goldbert, Almqvist and Wiksell International, Stockholm pp. 456-468, 1981.

M. P. Hlastala: Multiple Inert Gas Elimination Technique, JAP: Respir Environ Exercise Physiol 56(1): 1-7, 1984.

Hlastala and Ralph: Interaction of Exhaled Gas with Airway Mucosa, Proceedings XXIX, Congress of the International Union of Physiological Sciences 15:304, 1983.

Robertson et al.: Respiratory and Inert Gas Exchange During High Frequency Ventilation, JAP: Respir Environ Exercise Physiol 51:683-689, 1982.

McEvoy et al.: Pulmonary Gas Exchange During High-Frequency Ventilation, JAP: Respir Environ Exercise Physiol 52:1278-1288, 1982.

A. W. Jones: Quantitative Measurements of Alcohol Concentration and the Temperature of Breath During a Prolonged Exhalation, ACTA, Physiologica Scandinavia 114:407-412, 1982.

McFadden et al.: Direct Recordings of the Temperature in the Tracheobronchial Tree in Normal Man, Journal of Clinical Investigation 69:700-705, 1982.

E. R. McFadden: Respiratory Heat and Water Exchange: Physiological and Clinical Implications, JAP: Respir Environ Exercise Physiol 54:331-336, 1983.

K. W. Dubowski: Breath Analysis as a Technique in Clinical Chemistry, Clinical Chemistry 20:966-972, 1982.

Levett and Karras: Errors in Current Alcohol Breath Analysis, Alcohol, Drugs and Traffic Safety, ed. by L. Goldberg, Almqvist and Wiksell International, Stockholm, 1981, pp. 527-532.

H. Rahn: A Concept of Mean Alveolar Air and the Ventilation-Blood Flow Relationships During Pulmonary Gas Exchange, Journal of Physiology, 153:21-30, 1949.

West and Dollery: Distribution of Blood Flow and Ventilation-Perfusion Ratio in the Lung, Measured with Radioactive $CO_2$, JAP: 15:405-418, 1960.

L. E. Farhi: Elimation of Inert Gas by the Lung, Respiratory Physiology 3:1-11, 1967.

W. S. Fowler: Lung Function Studies, III. Uneven Pulmonary Ventilation in Normal Subjects and in Patients with Pulmonary Disease, JAP 1:283-299, 1949.

Hlastala and Robertson: Inert Gas Elimination Characteristics of the Normal Lung, JAP: Respir Environ Exercise Physiol 44:258-266, 1978.

ISOTHERMAL REBREATHING APPARATUS AND METHOD

BACKGROUND OF THE INVENTION

1. Technical Field

The present invention relates generally to chemical analysis of human breath samples; and, more particularly, to apparatus and methods for collecting human breath samples for accurate analysis of their chemical content, in particular their ethyl alcohol content. The invention takes advantage of the fact that the ethyl alcohol content of the air located deep in the lungs (alveolar air) is found to be in equilibrium with the ethyl alcohol content of the blood; and, by utilizing the known mathematical constant relationship between the ethyl alcohol in the lungs and the blood alcohol concentration under equilibrium conditions, a determination of the exact blood alcohol content based on the content of ethyl alcohol in the lungs can be made.

As the ensuing description proceeds, those skilled in the art will appreciate that the present invention can be used in a wide variety of diverse applications such as: (i) in law enforcement for the analysis of blood alcohol in suspected drunk drivers; (ii) in medicine for the chemical analysis of human breath for the detection or treatment of disease; and (iii) in physiological evaluation of pulmonary dysfunction.

The foregoing potential applications for use of the present invention, however, are listed as representative only, and are not limitative of the scope of the present invention as reflected in the appended claims.

2. Background Art

In the law enforcement area, it is often necessary to determine the blood alcohol concentration in units of percent weight by volume of persons suspected of driving while intoxicated (DWI). Testing of the blood alcohol content of suspected drunk drivers is not new; however, the public attitude towards drunk driving has changed in recent years from that of general apathy to an attitude of anger and concern. The public has now realized a large percentage of fatal automobile accidents are caused by drunk drivers. Groups such as Mothers Against Drunk Drivers (MADD) have organized on a national level to pressure individual states and the federal government to adopt tougher drunk driver laws. The success of the anti-drunk driving lobbies has been evidenced recently by the trend of many states to raise the alcohol drinking age to twenty-one years old. In addition, many states are requiring mandatory jail sentences for individuals convicted of firsttime drunk driving offenses. Newspapers and magazines are giving increased publicity to the vehicular death and destruction caused by drunk drivers, and to the recent legislation enacted to discourage drunk driving. State governors are using tough anti-drunk driving stances as a major campaign issue. Tough drunk driving laws have been enacted and enforced in Europe, Japan, and other countries for years; however, in the United States, this is a relatively recent phenomena.

With the prospect of jail and/or large fines facing those charged with drunk driving offenses, defendants are fighting back in court with renewed vigor. Their attack is aimed at the cornerstone of the DWI charge—viz., the accuracy of the blood alcohol test itself, and the competency of the personnel administering these tests. Obviously, the most accurate test that could be employed is analysis of a blood sample per se; but, such a test is invasive and, therefore, generally a test that cannot be utilized absent the subjects "informed consent". Therefore, the blood alcohol test most often used by law enforcement authorities involves a relatively easy-to-use, low cost, non-invasive procedure—viz., the "Breathalizer" which is based upon non-invasive analysis of a breath sample to determine the content of ethyl alcohol in the bloodstream. It is for this reason that the accuracy of the breath test for alcohol content is coming under the heaviest attack from defendants charged with driving while intoxicated.

The average human lung contains approximately 300 million small air sacs called "alveoli" which are surrounded by blood vessels. The alveoli of the lung are connected to the mouth by the trachea and a tree-like array of airways which allow for the movement of air from outside the subject's body to the alveoli in the lung. The major function of the lung is to allow for the exchange of oxygen and carbon dioxide between the blood and air within the lung. It has generally been accepted that the air content of the lung is an optimal point for measuring the amount of alcohol in the blood because the membranes of the lung are thin enough to allow rapid exchange of the alcohol between the blood and the air within the lung gas. Therefore, even though it is impossible to measure the amount of alcohol within the alveolar gas, the partial pressure of alcohol within the lung is believed to be the same as that in the blood under equilibrium conditions. Therefore a major assumption is made that the alcohol concentration in the exhaled breath, after the dead space is exhaled, is a constant value and equal to the blood value. It is also assumed that the breath alcohol concentration is equal to the lung air alcohol concentration.

The fact that the blood perfusion (flow) rate in the vessels surrounding the alveoli may vary has been known for years (References 18, 19). For most gases eliminated by the lung, the variation in matching alveolar ventilation and perfusion results in large variations of alveolar gas partial pressure (Reference 20). However, for a gas with a very high partition coefficient, such as ethyl alcohol, the variation in alveolar partial pressure due to differences in alveolar ventilation and perfusion matching is virtually eliminated (Reference 22). Therefore the expected single breath partial pressure profile for ethyl alcohol is essentially flat.

There is a difference, however, in the actual concentration of alcohol molecules within the gas contained in the lung (hereinafter referred to as "alveolar gas") compared to the concentration of alcohol molecules in the bloodstream. This difference is described by a mathematical relationship called the "partition coefficient" which is defined as the concentration of alcohol in the bloodstream divided by the concentration of alcohol in the air of the lungs at a prescribed temperature. Therefore, if a breath sample in equilibrium with the blood in the lungs is obtained, the blood alcohol concentration may be derived from the breath alcohol content by multiplying the breath alcohol concentration by the partition coefficient.

The exact value of the partition coefficient, although vital to an accurate determination of the blood alcohol content, has been open to dispute. See, for example, B. M. Wright, *Breath Alcohol Analysis And The Blood/Breath Ratio*, MEDICAL SCIENCE LAW, Vol. 15, No. 3, pp. 20-207 (1975); and M. F. Mason and K. M. Dubowski, *Breath-Alcohol Analysis: Uses, Methods, and*

*Some Forensic Problems—Review and Opinion,* JOURNAL OF FORENSIC SCIENCE, Vol. 33, pp. 9–41 (1976). The most accurate determination of the partition coefficient, however, was found to be 1,756 at 37° C. See, A. W. Jones, *Determination of Liquid/Air Partition Coefficient for Dilute Solutions of Ethanol in Water, Whole Blood and Plasma,* JOURNAL OF ANALYTICAL TOXICOLOGY, Vol. 7, July/August, pp. 193–197 (1983). Therefore, the partition coefficient of 2100 currently used in most breath tests results in calculated blood alcohol concentrations that are erroneously high by about twenty percent (20%).

Various techniques have been used in the past to determine blood alcohol content based upon the breath alcohol content including chemical processing, gas chromatography and infrared absorption techniques. Briefly, infrared absorption involves passing infrared waves of two discrete wavelengths within a discrete frequency band through a breath sample wherein the energy at each wavelength is measured after exiting the breath sample to determine the amount of energy absorbed at each wavelength by the molecules in the breath sample. These absorption values are then compared to known values for the absorption of ethanol and other gases at various concentrations to allow determination of the amount of ethyl alcohol in the sample tested. U.S. Pat. No. 4,268,751—Fritzlen et al discusses the use of two wavelengths of infrared energy at 3.48 microns and 3.3 microns to determine the presence of both ethanol and acetone in a breath sample. Previously, a single wavelength of 3.39 microns was utilized; but, both ethanol and acetone absorb infrared energy at this wavelength. However, since their absorption amounts differ relatively at discrete wavelengths 3.39 microns and 3.48 microns, the presence of both ethanol and acetone in the sample may be detected based upon the relative absorption of the infrared energy at these two frequencies.

For further clarification, additional descriptions of the apparatus and procedures used in infrared analysis are discussed in Harte, U.S. Pat. No. 3,792,272 and Adrian, U.S. Pat. No. 4,057,724.

A further listing of work carried out in the area of breath alcohol analysis is provided as follows:

1. R. N. Harger, R. B Forney and R. S. Baker, *Estimation of the Level of Blood Alcohol from Analysis of Breath II, Use of Rebreathed Air,* JOURNAL OF STUDIES IN ALCOHOL, Vol. 17, pp. 1–18 (1956);
2. A. W. Jones, *How Breathing Technique Can Influence the Results or Breath—Alcohol Analysis,* MEDICAL SCIENCE LAW, Vol. 4, No. 4, pp. 275–280 (1982);
3. A. W. Jones, *Effects of Temperature and Humidity of Inhaled Air on the Concentration of Ethanol in a Man's Exhaled Breath,* CLINICAL SCIENCE, Vol. 63, pp. 441–445 (1982);
4. A. W. Jones, *Role of Rebreathing in Determination of the Blood-Breath Ratio of Exhaled Ethanol,* JOURNAL OF APPLIED PHYSIOLOGY: RESPIRATION, ENVIRONMENTAL AND EXERCISE PHYSIOLOGY, Vol. 55, pp. 1237–1241 (1983);
5. J. C. Russell and R. L. Jones, *Breath Ethyl Alcohol Concentration and Analysis in the Presence of Chronic Obstructive Pulmonary Disease,* CLINICAL BIOCHEMISTRY, Vol. 16, No. 3, pp. 182–187 (1983);
6. J. Schwartz, C. Pinkward and A. Slemeyer, *Ein nueues Verfahren zur Bestimmung des Blutalkoholgehaltes uber die Atemluft bei Bewusstlosen,* (A New Method to Estimate Blood Alcohol Concentration From the Breath of Unconscious Subjects), ANAESTHETIST, Vol. 31, pp. 177–180 (1982);
7. A. Slemeyer, *Analytical Model Describing the Exchange Processes of Alcohol in the Respiratory System,* ALCOHOL, DRUGS AND TRAFFIC SAFETY, ed. by L. Goldberg, Almqvist and Wiksell International, Stockholm, pp. 456–468 (1981);
8. M. P. Hlastala, *Multiple Inert Gas Elimination Technique,* JOURNAL OF APPLIED PHYSIOLOGY: RESPIRATION, ENVIRONMENTAL AND EXERCISE PHYSIOLOGY, Vol. 56, No. 1, pp. 1–7 (1984);
9. M. P. Hlastala and D. D. Ralph, *Inter-action of Exhaled Gas with Airway Mucosa,* PROCEEDINGS XXIX CONGRESS OF THE INTERNATIONAL UNION OF PHYSIOLOGICAL SCIENCES, Vol. 15, p. 304 (1983);
10. H. T. Robertson, R. L. Coffey, T. A. Standaert and W.E. Truog, *Respiration and Inert Gas Exchange During High Frequency Ventilation,* JOURNAL OF APPLIED PHYSIOLOGY: RESPIRATION, ENVIRONMENTAL AND EXERCISE PHYSIOLOGY, Vol. 51, pp. 683–689 (1982);
11. R. D. McEvoy, N. J. H. Davies, F. L. Mannino, R. J. Prutow, P. T. Schumaker, R. D. Wagner and J. B. West, *Pulmonary Gas Exchange During High-Frequency Ventilation,* JOURNAL OF APPLIED PHYSIOLOGY: RESPIRATION, ENVIRONMENTAL AND EXERCISE PHYSIOLOGY, Vol. 52, pp. 1278–1288 (1982);
12. A. W. Jones, *Quantitative Measurements of the Alcohol Concentration and the Temperature or Breath During a Prolonged Exhalation,* ACTA. PHYSIOLOGICA SCANDINAVICA, Vol. 114, pp. 407–412 (1982);
13. E. R. McFadden, D. M Denison, J. F. Walker, B. Assoufi, A. Peacock, and T. Sopwith, *Direct Recordings of the Temperature in the Tracheobronchial Tree in Normal Man,* JOURNAL OF CLINICAL INVESTIGATION, Vol. 69, pp. 700–705 (1982);
14. E. R. McFadden, *Respiratory Heat and Water Exchange: Physiological and Clinical Implications,* JOURNAL OF APPLIED PHYSIOLOGY: RESPIRATION, ENVIRONMENTAL AND EXERCISE PHYSIOLOGY, Vol. 54, pp. 331–336 (1983);
15. K. M. Dubowski, *Breath Analysis As A Technique In Clinical Chemistry,* CLINICAL CHEMISTRY, Vol. 20, pp. 966–972, 1982.
16. M. F. Mason and K. M. Dubowski, *Breath-Alcohol Analysis: Uses, Methods, and Some Forensic Problems—Review and Opinion,* JOURNAL OF FORENSIC SCIENCE, Vol. 33, pp. 9–41 (1976);
17. J. Levett and L. Karras, *Errors in Current Alcohol Breath Analysis,* ALCOHOL, DRUGS AND TRAFFIC SAFETY, ed. by L. Goldberg, Almqvist and Wiksell International, Stockholm, pp. 527–532 (1981);
18. H. Rahn, *A Concept of Mean Alveolar Air and the Ventilation-Blood Flow Relationships During Pulmonary Gas Exchange,* JOURNAL OF PHYSIOLOGY Vol. 153, pp. 21–30 (1949);
19. J. B. West and C. T. Dollery, *Distribution of Blood Flow and Ventilation-Perfusion Ratio in the Lung,*

*Measured With Radioactive CO₂*, JOURNAL OF APPLIED PHYSIOLOGY, Vol. 15, pp. 405–418 (1960);

20. L. E. Farhi, *Elimination of Inert Gas by the Lung*, RESPIRATION PHYSIOLOGY, Vol. 3, pp. 1–11 (1967);

21. W. S. Fowler, *Lung Function Studies III. Uneven Pulmonary Ventilation in Normal Subjects and in Patients With Pulmonary Disease*, JOURNAL OF APPLIED PHYSIOLOGY, Vol. 1, pp. 283–299 (1949); and, 22. M. P. Hlastala and H. T. Robertson, *Inert Gas Elimination Characteristics of the Normal Lung*, JOURNAL OF APPLIED PHYSIOLOGY: RESPIRATION, ENVIRONMENTAL AND EXERCISE PHYSIOLOGY, Vol. 44, pp. 258–266 (1978).

In most current breath-testing apparatus, the subject is required to breathe directly into a gas analyzer, such as an infrared analyzer described previously, which utilizes a sample from the end of the breath for analysis, hereinafter referred to as the "end-expired breath method". This method allows for the exhalation of a sufficient amount of breath gases to eliminate any air in the mouth and trachea which are assumed to have little or no alcohol content—that is, so-called "dead space gas"—such that the sample of alveolar gas is taken from the latter part of the exhaled breath. The end-expired breath method assumes that the alcohol concentration of the exhaled breath after elimination of the dead space gas is a constant value and proportional to the blood alcohol content.

Recently, however, it has been shown that the alcohol concentration in the breath is not constant but, rather, changes continuously as the subject exhales. See, e.g., Reference Nos. 1 through 7, supra. In the majority of studies, in fact, the alcohol concentration was found to increase as the subject exhaled. To explain this phenomenon, recent observations have found that highly soluble gases interact with the subject's airways during inhalation and exhalation. See, e.g., Reference Nos. 9 through 11 supra. During inhalation, as the inhaled cooler air from the outside is brought into the lungs, it is warmed by the transfer of heat from the tissues of the subject's airways. See, e.g., Reference Nos. 12 through 14, supra. The heat transfer between the subject's airways and the inhaled/exhaled breath results in partial condensation of alcohol over the tissues of the airway, changing the concentration of ethyl alcohol in the breath.

Early studies of the end-expired breath method of breath analysis have produced data which bear reasonable correlation to the concentrations of ethyl alcohol obtained through blood sample tests. Because of changing breath alcohol concentrations, however, random breath samples yielded average values which correlated to the blood sample concentration even though variations as much as fifty percent (50%) occurred in individual measurements. See, e.g., Reference Nos. 16 and 17, supra. These measurements were made, however, by instruments which ignored the interaction of breath alcohol with the tissue of the subject's airway.

The article by A. W. Jones entitled *"The Role of Rebreathing in Determination of the Blood/Breath Ratio of Expired Ethanol"* (Reference No. 4), discloses that temperature gradients between the subject's lungs and mouth result in the exchange of water-soluble agents such as ethyl alcohol with the walls of the subject's airways resulting in inaccurate measurements when the end of the expired breath was analyzed. Jones indicates, however, that the concentration of ethyl alcohol in end-expired air will be less than that found in the alveolar gas. Jones utilized a rebreathing procedure to reduce the temperature gradient across the airways and trachea in an attempt to achieve a steady state breath temperature of approximately 35.2° C., which then was mathematically adjusted to 37° C., in an attempt to provide a more accurate estimation of the alveolar level of ethyl alcohol. This mathematical adjustment was based upon a supposed linear relationship between expired breath temperature and the blood/breath partition coefficient. Jones' mathematical adjustment to 37° C. is inaccurate however, because the airways and trachea comprise a dynamic system where equilibrium conditions do not exist. Jones' rebreathing technique required the subject to breathe into a heated polyethylene bag one to five times, with the final exhalation made into a separate breath analyzing instrument which recorded the breath temperature, exhaled volume and breath alcohol concentration.

In addition to the foregoing problems, those skilled in the art have experienced many other significant problems when attempting to collect breath samples for chemical analysis. Due to the high vapor content of typical breath samples collected, there is a substantial likelihood of condensation of such vapor onto the walls of the sample collecting receptable resulting in additional inaccuracies.

In the aforementioned article by R. N. Harger et al entitled *"Estimation of the Level of Blood Alcohol From Analysis of Breath—Use of Rebreathed Air"* (Reference No. 1), a polyethylene bag was utilized for a rebreathing procedure. In an attempt to eliminate any moisture condensation within the sample bag, the bag was initially placed inside an incubator sack heated to 45°–50° C., remaining inside until the sample bag reache a temperature of approximately 45° C. The bag was then removed from the incubator sack; the subject rebreathed five times into the bag; the bag was then returned to the incubator sack and evacuated to a sampling ampule tube. A disadvantage with Harger's method of preventing condensation is that the temperature of the breath sample inside the bag is neither measured nor controlled when the sample bag is outside the incubator sack. Therefore the temperature of the breath sample may fall below the dew point temperature causing condensation within the sample bag.

Additional problems occurring when using conventional breath collection methods and apparatus include the resistance offered by a narrow breathing tube to the flow of exhaled air therethrough, a so-called "back pressure". This back pressure increases the alveolar pressure making it difficult for people with lung diseases or defects to provide a breath sample of sufficient volume to include air from the deep lung area. The problem is further exacerbated by the fact that the increased alveolar pressure causes an alteration in the pattern of emptying the lungs resulting in differences in alcohol concentration in the breath sample.

Although it has been recognized that temperature gradients within the mouth, trachea and airways introduce errors into the determination of blood alcohol content from breath sample analysis, conventional methods and apparatus as described in the aforesaid references have failed to achieve a solution for eliminating the problems induced by such temperature gradients. Nor have such conventional systems provided solutions for the aforesaid condensation and back pressure problems. Therefore, prior to the advent of the present invention, there has remained an urgent need for improved methods and apparatus for determining the blood alcohol content from a breath sample which can be collected and analyzed at the proper temperature and which overcomes the problems associated with condensation and resistance to the subject's exhaled breath.

SUMMARY OF THE INVENTION

Accordingly, it is a general aim of the present invention to provide an improved apparatus and method for collecting breath samples for chemical analysis of their ethyl alcohol content, an apparatus and method which is characterized by its improved accuracy, ease of use, and decreased breathing resistance, and which overcomes all the foregoing disadvantages inherent in conventional apparatus and methods.

In one of its more detailed aspects, it is an object of the present invention to provide an improved apparatus and method for collecting breath samples under isothermal rebreathing conditions resulting in thermal equilibrium between the breath sample and the subject's airway tissues, characterized in that the breath samples are collected in an enclosed, flexible, variable volume, baglike receptacle which includes means, such as for example, a mouthpiece in communication with the interior space of the sample bag, to permit a human subject to repetitively exhale into and inhale from the sample bag while the breath sample within the bag is maintained at or near the subject's body temperature. Suitable means for maintaining the sample bag at a temperature in substantial equilibrium with the subject's body temperature includes a closed, airtight heating chamber enclosing the sample bag and including therein means, such as a heating coil or incandescent light, for heating the inside of the container and the sample bag contained therein. Sensing means, such as a temperature probe, are utilized to determine the temperature of the breath sample and in the sample bag and to relay the temperature information to an automatic electronic controller, such as a software controlled microcomputer, or human operator, to compare the temperature information relayed from the probe to a reference level established by either a software program, input from a human operator, or measurement of the subject's body temperature, in order to regulate the output of the heating means within the heating container. The optimum breath sample for accurately determining blood alcohol content is obtained when the temperature of the rebreathed breath sample is at or near the temperature of the subject's airway passages, normally 98.6° F. or 37° C. Sensing means are positioned in close proximity to the sample bag inlet to obtain the most accurate breath temperature information. Means for extracting the breath sample from the sample bag for subsequent chemical analysis of the ethyl alcohol content utilize an extraction conduit in fluid communication with the sample bag; the pressure inside the evacuation conduit is reduced to about 200 mm Hg by a vacuum or parastoltic pump wherein the breath sample is evacuated to a sample gas analyzer which uses conventional analysis methods such as infrared analysis to determine the ethyl alcohol content.

The improved apparatus and methods of the present invention facilitate collection of a breath sample which provides for a more accurate representation of the subject's blood alcohol content wherein the heating chamber is interconnected and in fluid communication with a second variable volume or bellows-like chamber such that the volume of the bellows chamber increases as the sample bag inflates and decreases as the sample deflates to permit the sample bag to inflate and deflate inside an enclosed, airtight container thereby maintaining improved temperature constancy around the sample bag. Stated another way, the heating chamber includes a first chamber portion for enclosing the sample bag, a second variable volume change portion, and conduit means interconnecting the first and second chamber portions for permitting fluid communication therebetween as the volume of breath gases contained within the sample bag is cyclically increased and decreased as the subject exhales into and inhales from the sample bag.

Further improvements in temperature constancy are obtained utilizing means, located upstream of the sample bag, for preheating the breath sample to the desired temperature wherein the preheater means comprise a number of electrical resistance heating elements located in a conduit interconnecting the mouthpiece with the sample bag, the heating elements forming a grid-like pattern across the conduit passageway. An electronic sensor located on the heating grid relays the temperature of the breath sample to a central controller to regulate the temperature of the heating grid.

It is a further and more detailed object of the present invention to minimize any internal breathing resistance of the isothermal breathing apparatus in order to facilitate obtaining breath samples of sufficient volume from subjects experiencing breathing impediments wherein the conduit interconnecting the mouthpiece to the sample bag has an internal diameter of approximately one inch.

DESCRIPTION OF THE DRAWINGS

These and other objects and advantages of the present invention will become more readily apparent upon reading the following detailed description and upon reference to the attached drawings, in which.

While the present invention is susceptible of various modifications and alternative forms, specific embodiments thereof have been shown by way of example in the drawings and will herein be described in detail. It should be understood, however, that it is not intended to limit the invention to the particular forms disclosed, but, on the contrary, the intention is to cover all modifications, equivalents and alternatives falling with the spirit and scope of the invention as expressed in the appended claims.

DETAILED DESCRIPTION

As indicated previously, various studies have been conducted which indicate that when utilizing a breath sample taken at the end of the subject's exhaled breath, errors due to the interaction of heat and alveolar gases with the tissues of the subject's airways results. To confirm these findings, the following experiment was performed.

EXAMPLE I

Five human subjects drank a sufficient quantity of Scotch Whiskey to bring their blood alcohol level to between 0.06 and 0.14 gram percent as documented by the blood samples analyzed by either the clinical chemistry laboratory at Harborview Medical Center (Washington State Toxicologists Lab) or the University of Washington Hospital in Seattle. After waiting for at least 60 minutes after ingesting the alcohol, the subjects breathed into a standard mouthpiece from room air at 20° C., at an exhalation flow rate of approximately 0.5 liters per second; the subjects making one complete exhalation in accordance with the standard method practiced by law enforcement personnel for "Breathalizer" testing. The mouthpiece was connected to a wedge spirometer, manufactured by Med-Science Company, St. Louis, Mo., which read out the volume of air exhaled and flow rate of exhaled air to an 8-channel recorder made by Hewlett-Packard, Waltham, Mass. The signals to the recorder were processed with a Sanborn preamplifier and analog low-pass filters having a roll-off frequency of 10 Hz to remove radio frequency interference. The concentrations of ethyl alcohol and carbon dioxide were recorded continuously on separate channels of the recorder. There was no interference from acetone. Using a Model QMG 511 quadrupole mass spectrometer manufactured by Balzers Corporation, Balzers, Liechtenstein, measurements of the breath alcohol content were made continuously during the entire duration of the exhaled breaths. The mass spectrometer was controlled by a Model PDP 11/34 digital computer manufactured by Digital Equipment, Maynard, Mass. Over the past three years, it has been shown that for all gases measured, Balzers' mass spectrometer is accurate to within two percent (2%) of the actual concentration of the gas in the blood. The mass spectrometer was calibrated to provide the calculated blood alcohol concentrations by extracting a portion of the blood sample with a syringe, allowing the sample to equilibrate at 37° C. for 45 minutes, separating the liquid and gas phases, analyzing the gas phase using the mass spectrometer, and analyzing the blood portion for use as a reference value using a gas chromatograph. The results of the tests from the five subjects were as follows:

| Subject | Measured Blood Alcohol Concentration (gm %) | Cumulative Volume of Exhaled Air (ml) | Calculated Blood Alcohol Concentration Based on Mass Spectrometer Readout (gm %) |
|---|---|---|---|
| 1 | .126 | 500 | .033 |
|   |      | 1000 | .082 |
|   |      | 1500 | .104 |
|   |      | 2000 | .116 |
|   |      | 2500 | .128 |
|   |      | 3000 | .140 |
|   |      | 3500 | .153 |
|   |      | 4000 | .165 |
|   |      | 4500 | .177 |
|   |      | 5000 | .189 |
| 2 | .060 | 500 | .007 |
|   |      | 1000 | .050 |
|   |      | 1500 | .057 |
|   |      | 2000 | .065 |
|   |      | 2500 | .070 |
|   |      | 3000 | .074 |
|   |      | 3500 | .077 |
|   |      | 4000 | .082 |
| 3 | .139 | 500 | .080 |
|   |      | 1000 | .111 |
|   |      | 1500 | .130 |
|   |      | 2000 | .148 |
|   |      | 2500 | .161 |
|   |      | 3000 | .173 |
| 4 | .113 | 500 | .015 |
|   |      | 1000 | .075 |
|   |      | 1500 | .109 |
|   |      | 2000 | .124 |
|   |      | 2500 | .137 |
|   |      | 3000 | .151 |
|   |      | 3500 | .155 |
| 5 | .106 | 500 | .021 |
|   |      | 1000 | .079 |
|   |      | 1500 | .098 |
|   |      | 2000 | .109 |
|   |      | 2500 | .117 |
|   |      | 3000 | .122 |
|   |      | 3500 | .127 |
|   |      | 4000 | .133 |

Figure 1:
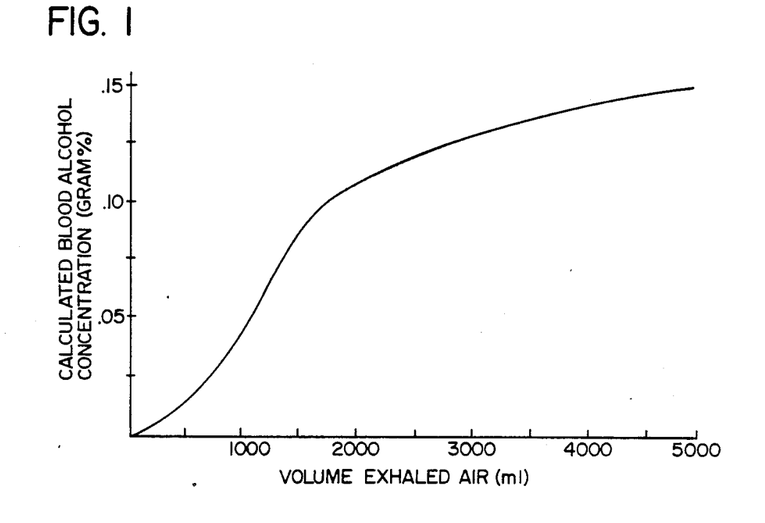
FIG. 1 is a graphical representation of breath alcohol concentration as a function of the expired volume of breath.

A curve representative of the above data graphically illustrated in FIG. 1 indicates that the breath alcohol concentration is not constant during exhalation. Rather, the data confirm the fact that as the subject exhales, the alcohol concentration gradually increases until a maximum value is reached near the end of the exhaled breath. The end-exhaled breath sample contains a concentration of alcohol sixty percent (60%) higher than that determined by blood sample analysis. This is in contrast to the initial portion of the exhaled breath which is up to fifty percent (50%) below the concentration determined by the blood sample analysis. As mentioned previously, it has been shown that the highly soluble breath gases interact with the tissues in the subject's airways during inhalation and exhalation. During inhalation, as the inspired air from outside is brought into the lung, it is warmed by the exchange of heat with the airways. The gas from the alveoli are cooled slightly during exhalation from a temperature of 37° C. in the lung to a temperature of 34° C. at the mouth. See, Reference No. 15.

Although not wishing to be bound by theory, it is believed that the subject's inhaled breath is warmed by the tissues of the airway, resulting in heat transfer thereto and a resultant cooling of the airway walls. Therefore, during the initial portion of exhalation, alveolar gas containing alcohol passes through the cooler airways, resulting in some cooling of the alveolar gas and subsequent condensation of the ethyl alcohol contained therein onto the surface of the airways. As exhalation continues, the airways begin to warm up, revaporizing this condensed alcohol, and increasing the concentration of alcohol in the exhaled gas.

To test the above theory, the following experiments were conducted:

EXAMPLE II

Utilizing the procedures of Example the alcohol concentration of the subjects' breath from a single inhalation was recorded as a function of time wherein time zero marked the beginning of the exhalation. Data which was obtained during the testing of one subject and representative of data obtained from the group of subjects is provided below:

| Time (sec) | Calculated Alcohol Concentration (gm %) | Time (sec) | Calculated Alcohol Concentration (gm %) | Time (sec) | Calculated Alcohol Concentration (gm %) |
|---|---|---|---|---|---|
| 0 | 0 | 11 | .087 | 22 | .124 |
| 1 | .005 | 12 | .091 | 23 | .126 |
| 2 | .014 | 13 | .096 | 24 | .129 |
| 3 | .026 | 14 | .100 | 25 | .132 |
| 4 | .037 | 15 | .103 | 26 | .134 |
| 5 | .048 | 16 | .107 | 27 | .136 |
| 6 | .057 | 17 | .110 | 28 | .138 |
| 7 | .065 | 18 | .112 | | |
| 8 | .072 | 19 | .116 | | |
| 9 | .077 | 20 | .118 | | |
| 10 | .082 | 21 | .121 | | |

Figure 2:
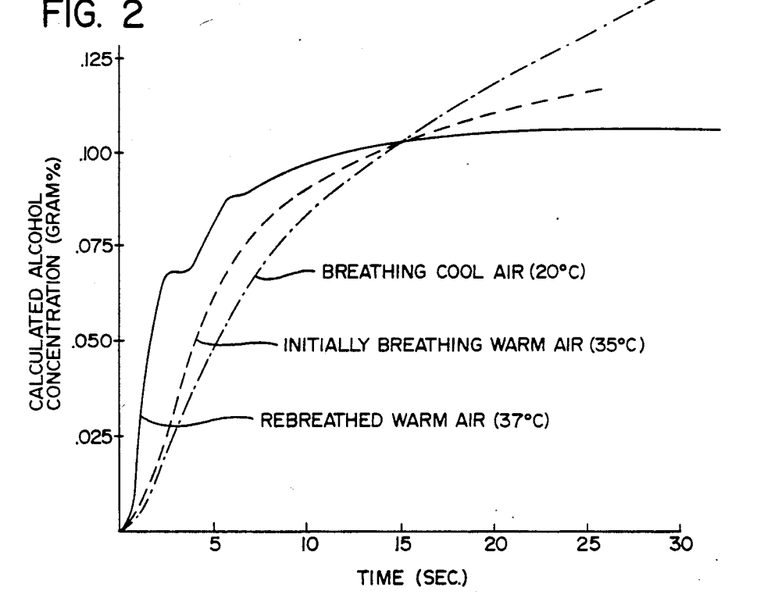
FIG. 2 is a graphical representation of the breath alcohol concentration as a function of time wherein there is compared breath samples obtained from (i) first inhaling cool air (20° C.), (ii) first inhaling three breaths of warmed air (35° C.), and (iii) rebreathing warmed air (37° C.); and wherein time zero for sample runs at 20° C. and 35° C. commenced after the initial breath cycles of cool air or warm air were completed.

The above data graphically illustrated in FIG. 2 by a dashed-dotted line indicates that the breath alcohol concentration is rapidly increasing after 20 seconds of exhalation when 20° C. air is breathed.

EXAMPLE III

The procedure of Example I was followed except that the subjects initially took three breaths of air warmed to approximately 35° C. by a portable hair dryer. The alcohol concentration of a single exhaled breath was recorded as a function of time with time zero beginning after the three initial breath cycles of warmed air were taken. Data which was obtained during the the testing of pne subject and representative of data obtained from the group of subjects is provided below:

| Time (sec) | Calculated Alcohol Concentration (gm %) | Time (sec) | Calculated Alcohol Concentration (gm %) | Time (sec) | Calculated Alcohol Concentration (gm %) |
|---|---|---|---|---|---|
| 0 | 0 | 11 | .093 | 22 | .114 |
| 1 | .005 | 12 | .095 | 23 | .115 |
| 2 | .016 | 13 | .098 | 24 | .116 |
| 3 | .032 | 14 | .100 | 25 | .117 |
| 4 | .048 | 15 | .102 | 26 | .117 |
| 5 | .059 | 16 | .104 | 27 | .118 |
| 6 | .069 | 17 | .106 | 28 | .119 |
| 7 | .076 | 18 | .108 | 29 | .120 |
| 8 | .081 | 19 | .109 | | |
| 9 | .086 | 20 | .111 | | |
| 10 | .089 | 21 | .112 | | |

The above data graphically illustrated in FIG. 2 by a dashed line indicates that the change in breath alcohol concentration after 20 seconds of rebreathing is reduced when warm (approximately 35° C.) air is initially breathed.

As discussed previously, the basic premise for determining blood alcohol content based on the concentration of alcohol in the alveolar gases of the lung is the fact that the blood alcohol is in equilibrium with the alveolar alcohol due to the rapid exchange of the alcohol between the blood and the gases in the lungs (alveolar gas) which occurs at the subject's body temperature. At equilibrium, the relative quantity of alcohol molecules in the blood at body temperature (normally 37° C.), although much greater than the quantity of alcohol molecules in the air, is a constant value under the conditions of body temperature and equilibrium—this relative quantity is termed the "partition coefficient". As the temperature varies from 37° C., such as, for example, where it is normally 34° C. at the mouth, the partition coefficient is no longer valid because the coefficient is based upon an equilibrium airway temperature of 37° C. whereas the sample breath collected may be at 35° C. or even lower. A mathematical correction of the breath alcohol concentration measured at 35° C. to the body temperature of generally 37° C. is not accurate because of the disequilibrium present due to the interchange of alcohol with airway tissues when the breath sample is not at body temperature.

In accordance with one of the more important aspects of the present invention, an isothermal rebreathing system is provided wherein provision is made for insuring that inhaled air and exhaled breath at all locations in the rebreathing system ranging from the deepest regions of the subject's lungs, through the various internal human airways and trachea to the mouth, and within the breath sample collection bag, was brought to, and maintained at, temperature equilibrium—generally at the subject's actual body temperature which, in the case of normal temperature, is near 37° C. (98.6° F.)—prior to actual collection of the end-expired breath for analysis. In the present invention, body temperature (which normally varies from 37° C.) will be measured with a probe placed sublingually (under the tongue). In the exemplary system, this is accomplished by rebreathing air from an enclosed air collection system which will not interact with ethyl alcohol and which is heated to 37° C. (or to the subject's actual body temperature in those instances where the subject's body temperature is other than normal). As a consequence of operation at conditions of temperature equilibrium between the tissue temperature in the subject's rebreathing system and the air being inhaled/exhaled, there is no tendency for heat transfer between tissue and air; and, consequently, alcohol in the alveolar gases being exhaled does not condense out and/or revaporize during the breathing cycle, and the alcohol concentration in the end-expired breath remains in equilibrium with the blood alcohol concentration.

Figure 3:
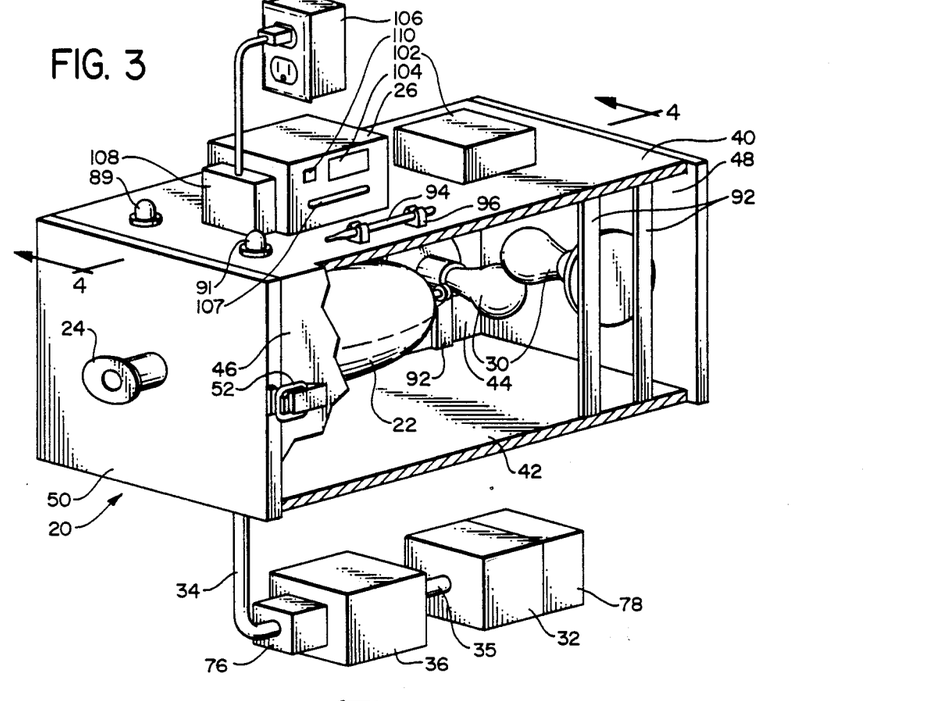
FIG. 3 is a highly diagrammatic perspective view of an isothermal rebreathing system embodying features of the present invention, here illustrating the breath sample bag, heating container, suction pump and motor, gas analyzer, and electrical power outlet.
Figure 4:
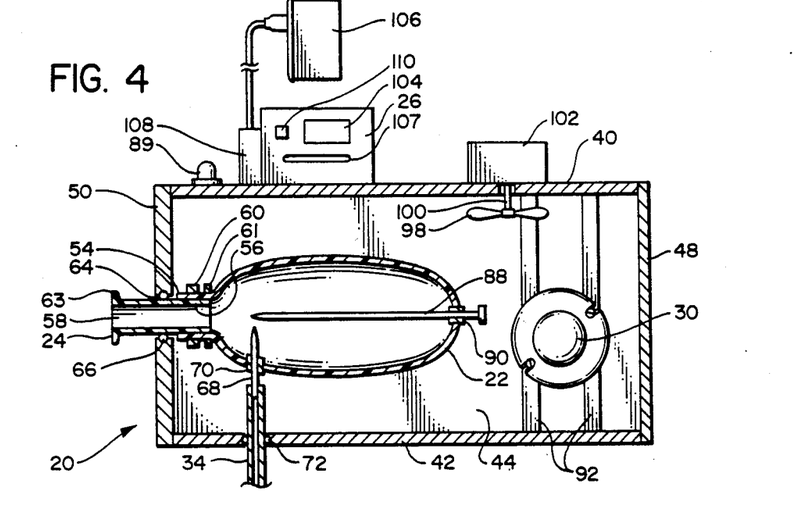
FIG. 4 is a front cross-sectional view taken substantially along the line 4—4 in FIG. 3, here depicting details of the heating container and breath sample bag.

Referring now to FIGS. 3 and 4, there has been diagrammatically illustrated an isothermal rebreathing system broadly comprising a heating container, generally indicated at 20, enclosing a bag-like sample receptacle 22 for the collection of exhaled air from a human subject through a mouthpiece 24 wherein bag 22 is held at a preset constant temperature by means of an electronic controller 26 positioned atop heating container 20. Controller 26 serves to activate suitable heating means 30, located inside heating container 20 and mounted on the sides thereof. Controller 26 includes, but is not limited to, the following principal components (not shown) for controlling heaters 30 and other parts of the isothermal rebreathing system to be described hereinbelow: a microprocessor, programmable read only memory (PROM), random access memory (RAM) and input/output devices. It should be appreciated that the operation of these components as well as the software controlling their operation is within the scope of one having ordinary skill in the art and will not be described further.

The breath sample is evacuated by a suction pump 32 via a conduit 35 interconnecting suction pump 32 and a sample collecting chamber (not shown) inside a sample gas analyzer 36. A conduit 34 projecting from the lower portion of the sample bag 22 through the lower portion of the heating container 20 conducts the breath sample to sample gas analyzer 36 for analysis of the chemical composition of the breath sample such as by infrared analysis.

In carrying out the present invention, the exemplary heating container 20 depicted in the drawings includes upper and lower walls 40, 42, sidewalls 44, 46, and an endwall 48, defining an essentially closed airtight container having a hinged access door 50 at the end opposite endwall 48. To permit observation of the interior or container 20, one or more of the walls 40, 42, 44, 46, 48 may be formed of transparent plastic material, glass, or the like. To maintain a closed, sealed airtight chamber, a conventional gasket (not shown) is preferably positioned at the interface between door 50 and the proximal ends of walls 40, 42, 44, 46. The sample bag 22, located inside heating container 20, preferably comprises a cylindrical, flexible bag-like receptacle approximately two liters in volume to accommodate the subject's lung capacity, and made of a material which is nonreactive with ethyl alcohol, which has good thermal conductivity, and which is relatively inexpensive so as to allow disposal of the bag after a breath sample has been collected, a material, such as, for example, polyvinylchloride or polytetraflouroethylene. In the illustrative form of the invention, the sample bag 22 includes an open neck 54 at the proximal end thereof for the receipt of a stem 56 integral with the mouthpiece 24; while mouthpiece 24 includes a passageway 58 to permit flow of sample gases from the subject's lungs to the interior of sample bag 22. In order to secure the mouthpiece 24 to stem 56 and bag 22, a locking collar 60 is provided which circumscribes neck 54 of bag 22 so as to securely secure neck 54 to stem 56. Mouthpiece 24 may comprise any suitable inexpensive, pliable plastic material which is non-reactive to ethyl alcohol, which fits into the subject's mouth and which is disposable after the breath sample has been collected.

In order to seal the contents of the sample bag 22 from the outside atmosphere when the prescribed breath sample temperature has been reached and the subject has finished supplying a breath sample and removed his mouth from mouthpiece 24, a clamping means 61, such as, for example, a spring clip, may be manually affixed about stem 56, such as when stem 56 is made of a sufficiently pliable material, for example rubber or the like, to close passageway 58 to the atmosphere. If, however, it is desired to have the above clamping operation proceed automatically, clamping means 61 may comprise an electronically actuated relay (not shown) via controller 26 to open and close a valve (not shown) located within passageway 58.

Mouthpiece 24, including a circumferential ridge 63 configured to fit inside the subject's mouth between the subject's lips and gums providing an airtight seal therebetween, is positioned proximate the top of access door 50 such that the subject's eyes and nose are above and clear of access door 50. In order to reduce the alveolar pressure buildup caused by forcing large volumes of exhaled air through passageway 58, passageway 58 is sized approximately one inch in diameter so as to allow normal exhalation. In addition, this allows those subjects with limited lung capacity due to physical defects or disease to exhale a sufficient volume of breath into sample bag 22 to obtain an accurate sample. To provide an airtight seal with the door 50, the stem 56 is inserted through an aperture 64 formed in the door 50 and is held in place by an O-ring seal 66 positioned within the aperture 64 to form an airtight friction fit. It should be appreciated that the mouthpiece 24 is easily removed from both door 50 and sample bag 22, thereby allowing disposal of mouthpiece 24 and sample bag 22 before collecting a new breath sample from another subject. It should also be apparent to those skilled in the art that the sample bag 22 and heating container 20 may be formed of different sizes, shapes and materials and still perform the broad objectives of the present invention as long as certain features are included such, for example, as: (i) the ability for heating container 20 to achieve sufficient temperature levels to heat the contents of the sample bag 22 to temperatures on the order of 37° C.; (ii) the provision of a sample bag 22 which is nonreactive with those gases introduced therein; and (iii), the provision of a sample bag 22 having thermal conductivity characteristics sufficient to insure adequate heating of the gases contained therein.

To permit routing of the breath sample contained within the sample bag 22, a sample collecting needle 68 extends through a septum 70 in the lower portion of sample bag 22 and passes into the interior thereof, as best illustrated in FIG. 2. The tip of a sample collecting needle 68 is located in close proximity to passageway 58 to extract the breath samples at or near the prescribed temperature. To this end, conduit 34 is coupled to sample collecting needle 68; conduit 34 extending through an O-ring seal 72 formed in the lower panel 42 of the heating container 20, thus maintaining an airtight fit therewith. Thus, the arrangement is such that the breath sample contained within the bag 22 comprising the equilibrated breath from the deepest regions of the subject's lungs is withdrawn under vacuum created by pump 32 to a removable sample collecting chamber (not shown) located within the sample gas analyzer 36 (FIG. 3); the sample collecting chamber sealable from the atmosphere in order to preserve the breath sample for later analysis. The sample gas analyzer 36 may be any of the conventional types commonly available in the marketplace such, for example, as the nondispersive infrared gas analyzer marketed by Andros Analyzers Inc., Berkeley, Calif., forms part of the present invention. Since such equipment is completely conventional and well known to persons skilled in the art, it will not be herein described in detail.

In carrying out the invention, provision made for withdrawing the sample gas contained in sample bag 22 utilizing a conventional parastoltic pump or vacuum pump 32 driven by motor 78—for example, the motor driven pump 32 may comprise a model PM 330 pump of the type manufactured by Medical Special Inc., Philadelphia, Pa.—and for routing the withdrawn sample to the sample collecting chamber in the sample gas analyzer 36 via collection needle 68, conduit 34, and a conventional pressure transducer 76 located downstream of collection needle 68.

Suction pump 32 is normally operated by controller 26 to maintain a pressure of approximately 200 mm Hg inside sample conduit 34 wherein the preset pressure established by controller 26 is continuously compared with the pressure sensed by transducer 76 to control the pressure drop created by pump 32. A pressure of 200 mm Hg prevents condensation of a typical breath sample in sample line 34 above 15° C. assuming the gas in sample bag 22 approaches 100% saturation at body temperature. It can be appreciated that any condensation of the sample gas will affect the relative concentration of ethyl alcohol delivered to the sample collecting chamber in the analyzer 36, thereby resulting in an erroneous analysis. At 200 mm Hg, the condensation temperature of water is sufficiently below room temperature to reduce the likelihood of accidental condensation. A heating blanket, not shown, comprising an electrical resistance heating element embedded within a thermally conductive, fire-resistant material may be placed around conduit 34 to prevent condensation therein.

A major premise of the rebreathing procedure is that the concentration of alcohol in the blood is directly related to the alveolar concentrations of ethyl alcohol in equilibrium with the ethyl alcohol in the blood. As discussed previously, there is a mathematical constant, the partition coefficient, which expresses the relationship between the ethyl alcohol content of the blood and the ethyl alcohol content of the air in the lungs. Although the blood flow (perfusion) rate in the blood vessels surrounding the alveoli may vary, the partition coefficient is independent of this perfusion rate. It should be appreciated, therefore, that a certain minimum volume of air per exhalation is necessary to obtain a breath sample which includes the alveolar gases and, therefore, which accurately reflects the blood alcohol content.

Figures 5, 6:
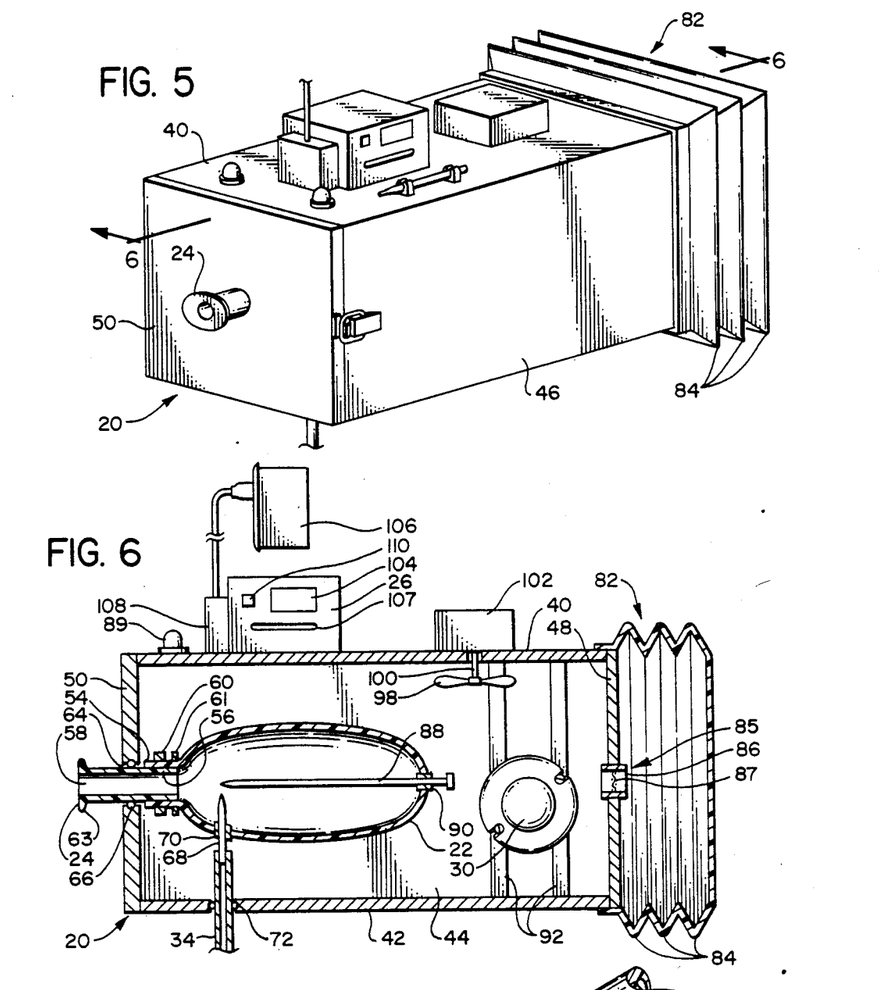
FIG. 5 is a perspective view of one embodiment of the present invention comprising a bellows section in operable communication with the heating container and sample bag receptacle.
FIG. 6 is a front cross-sectional view taken substantially along the line 6—6 in FIG. 5 here depicting an embodiment comprising the bellows section illustrated in FIG. 5; and, FIG. 7 is a perspective view of one embodiment of the present invention illustrating in phantom the breath preheating grid within the breathing mouthpiece.

In one embodiment of the present invention shown in FIGS. 5 and 6, a bellows section, generally indicated at 82, comprising bellows 84, is mounted at the distal end of the heating container 20. A flow measuring means generally indicated at 85, includes a conduit 86 located within and extending through endwall 48 of the heating container 20 in communication with both the interior of heating container 20 and bellows section 82. Conduit 86 includes a porous screen 87 across the inside thereof to impede the flow of air through tube 86, air which is dispelled from heating container 20 into bellows section 82 due to the expansion of sample bag 22 when filled with exhaled air from the subject. A differential pressure measuring means (not shown), such as for example a pressure transducer, in operable communication with screen 87 measures the pressure drop across screen 87 during the inhalation/exhalation cycle; and, that pressure drop, when integrated over time by controller 26, serves to permit calculation of the volume of air exhaled per breath, hereinafter referred to as "tidal volume". Utilization of bellows section 82 allows heating container 20 to remain closed from the atmosphere during rebreathing to insure sample bag 22 remains at the prescribed temperature. The values of pressure and tidal volume are displayed in digital form at controller 26. A minimum tidal volume required from the subject for an accurate breath sample is approximately 500 milliliters. The microprocessor controller 26 insures that the tidal volume is sufficient to obtain a valid sample.

In order to regulate the frequency and length of the subject's rebreathing cycles, indicator lights 89, 91 are mounted atop heating container 20 on upper wall 40 within the subject's field of vision. Indicators 89, 91 are lit for a predetermined length of time and at a predetermined frequency to guide the subject during the inhalation and exhalation portions of the rebreathing cycle, such that light 89 remains lit for a period of time over which the subject inhales, and light 91 remains lit for a period of time over which the subject exhales. Indicator lights 89, 91 are operated by controller 26 which is preprogrammed to activate lights 89, 91 at the proper frequency. In order to verify that the subject is breathing at the programmed rate, the rebreathing frequency of the subject is calculated by controller 26 using an internal counter (not shown) to count the number of times the breath flow pressure across screen 87 drops to zero from a positive flow pressure over a predetermined time interval. If the subject's rebreathing frequency varies a predetermined amount from the preprogrammed frequency, a message is displayed at LCD window 104 indicating an improper breathing frequency. Indicator lights 89, 91 may be labelled and color coded so that the subject is guided by the correct light in the rebreathing cycle.

Referring again to FIGS. 3 and 4, a temperature probe 88 is provided at the distal end of the sample bag 22 and serves to pierce a septum 90 formed in the bag 22, thus maintaining an airtight seal. Preferably, the tip of probe 88 is positioned in close proximity to the mouthpiece 24 and the sample collection needle 68 so as to enable continuous monitoring of the breath sample temperature by the controller 26. A plurality of heating means 30 (which may comprise resistance-type electrical heating elements or merely light bulbs) are mounted on vertical supports 92 at opposite sides of heating container 20, and provide sufficient thermal energy within heating container 20 to maintain a gas sample within the sample bag 22 at a preselected temperature.

An oral thermometer 94, secured by holder 96 in a friction fit therewith, is located atop heating container 20 and is provided for measuring the subject's actual body temperature which is input to the microprocessor controller 26. Thus, the thermometer 94, after being placed in the subject's mouth prior to obtaining a breath sample, provides the reference temperature—e.g., the subject's body temperature—which is input to the controller 26 for maintaining the temperature of the breath sample in the sample bag 22 in equilibrium with the subject's actual body tempeature.

In the illustrative embodiment of the present invention, the heaters 30 comprise one or more electric lights which are secured to vertical supports 92 and which are activated by controller 26. Thus, when utilizing a sample bag 22 having a volumetric capacity of approximately two liters, the heaters 30 serve to output at least 100 watts of power to maintain a temperature of 37° C.—viz., normal body temperature—inside sample bag 22, or, alternatively, to maintain temperature level in bag 22 which is equal to the actual body temperature of the subject, whether elevated above 98.6° F. (37° C.) or at a lower level. Electric lights are desirable in some instances because they can also provide an independent source of light which is useful when collecting breath samples in low light areas or at night. Heating coils may be utilized in place of electric lights when a more efficient source of heat is desired and the availability of an independent source of light is unimportant. Operation of heaters 30 is accomplished by controller 26 in conjunction with temperature probe 88 and thermometer 94. Thus, the subject's body temperature relayed from thermometer 94 is compared by controller 26 to the temperature relayed from probe 88, resulting in activation of the heaters 30 when the relayed temperature from probe 88 is below the subject's body temperature. Heaters 30 may be operated in a proportional mode wherein the current supplied to the heaters 30 is proportional to the deviation of the sample bag temperature from the subject's body temperature. As the amount of deviation increases, a potentiometer (not shown) operated by controller 26 increases the flow of current to heaters 30, thereby increasing the power output in the form of heat. In a second operating mode utilizing two or more heaters 30 which have lower individual power ratings than the heater described previously, constant current may be delivered to the heaters 30 until a temperature of about 1° C. or 2° C. below body temperature is reached, at which time the current is quickly terminated by controller 26 to all but one of the heaters 30. To raise the temperature of sample bag 22 to body temperature, the current of the remaining activated heater 30 is regulated by the potentiometer/controller pair until body temperature is reached, at which time the current is terminated, thereby reducing the amount of overshoot above body temperature due to the lower power output when using only one heater.

A rotating fan blade 98 positioned in proximity to the center of heating container 20 aids in the distribution of heated air about the sample bag 22 to insure a uniform temperature is maintained across the surface thereof. Fan blade 98 is mounted on the output shaft 100 of a suitable electric motor 102. Baffles (not shown) may be placed inside heating container 20 to assist fan 98 in circulating dead air for better heat distribution.

Overall control of the various system components described previously is maintained by controller 26, the microprocessor based microcomputer subsystem which includes a digital display which may be a liquid crystal display (LCD) or the like for displaying various temperatures and/or pressures at window 104 located on the face of controller 26. Controller 26 is responsible for receiving the following data:
1. Body temperature of the human subject as measured by thermometer 94;
2. Temperature of gases within sample bag 22 as measured by probe 88;
3. Pressure of sample gases through conduit 34 as measured by transducer 76;
4. Pressure differential of expelled air through conduit 86 measured by a pressure transducer;
5. Number of times breath flow pressure across screen 87 drops to zero;
6. Signals from analyzer 36.

Controller 26 controls the following operations:
1. Flow of current to heaters 30 in response to the difference in the subject's body temperature and the temperature of the breath sample inside sample bag 22.
2. Pressure drop created by suction pump 32 in response to the difference in pressure between the pressure set at the controller 26 and the pressure at transducer 76.

Controller 26 calculates and/or displays/prints out the following information:
1. Body temperature of the human subject;
2. Flow rate of subject's exhaled breath;
3. Volume of air per exhaled breath;
4. Blood alcohol concentration;
5. Rebreathinq frequency;
6. Information to assess adequacy of procedures.

Controller 26 utilizes an 16-bit microprocessor such as a Motorola 68000. Controller 26 includes an internal printer (not shown) for providing a hard copy of information through slot 107 located below window 104.

Electrical power requirements for the isothermal breathing system may be supplied from any 120 volt household supply or, alternatively, from a 12 volt car battery utilizing the cigarette lighter outlet inside the car. Electrical power is required for the operation of heaters 30, fan motor 102, suction pump motor 78, controller 26, pressure transducer 76, temperature probe 88 and the bellows pressure transducer.

Referring again to FIG. 1, electrical power is supplied from a power source illustrated as an outlet 106 connected to distribution bus box 108 adjacent to controller 26. Current flow from bus 108 to the fan motor 102, pump motor 78 and heaters 30 may be controlled by conventional electronic components such as various electronic filters to reduce any radio frequency interference (RFI); the specifics for connecting controller 26 to the previously mentioned components of the isothermal breathing system are well known to persons of ordinary skill in the art and, therefore, need not be further described herein.

Figure 7:
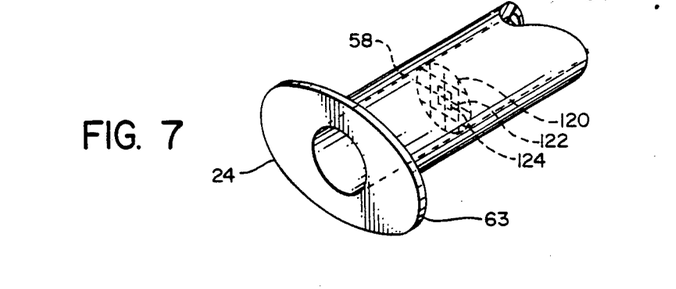

In one embodiment of the present invention shown in FIG. 7, a breath pre-heating means 120 is positioned across passageway 58 inside mouthpiece 24. The preheating means 120 comprises a honeycomb heating grid !22 made up of individual electrical resistance elements which when supplied with electrical current from controller 26 heat the breath sample flowing through passageway 58 nd across heating grid 122. A temperature detector 124, such as for example a thermocouple, attached near the center of grid 122 transmits the grid temperature to controller 26 for comparison with the reference temperature to maintain the proper grid temperature.

Operation of the isothermal rebreathing system proceeds as follows with reference to FIGS. 3 and 4: the system operator inserts the stem 56 of a sanitary, disposable mouthpiece 24 through aperture 64 in door 50, forming a friction, airtight seal therewith. A disposable sample bag 22 is mounted on stem 56 and held in place by collar 60 to form an airtight seal between the mouthpiece 24 and the sample bag 22. Door 50 is closed and latched shut. The system is turned on at controller 26 which goes through a preprogrammed self check of all components. Preprogrammed readouts (prompts) appearing at LCD window 104 direct the operator to obtain the subject's body temperature using thermometer 94. Body temperature data is processed by controller 26 which activates heaters 30 and fan motor 102 to warm the air inside sample bag 22 to a temperature level in equilibrium with the subject's actual body temperature—normally 37° C. (98.6° F.)—at which time the temperature is displayed in window 104 to prompt the operator to proceed with the sample collection The operator acknowledges the LCD prompt by pressing a "continue" key 110 on the controller 26, allowing the controller 26 to activate suction pump motor 78, thus reducing the pressure in sample line 34 to a predetermined value. The preset pressure is compared to the pressure relayed from flow measuring means 85 (FIG. 6), and when the two pressures match, the LCD window 104 displays the pressure relayed from flow measuring means 85, thus prompting the operator to proceed. The tidal volume of the subject's breathing is continually monitored by flow measuring means 85 such that if the tidal volume is less than the preset number, a prompt at LCD window 104 indicates an invalid sample. The subject is instructed to exhale through the mouthpiece 24 when indicator light 91 is lit, and then inhale through mouthpiece 24 when light 89 is lit; lights 89, 91 are activated so that the subject breathes at a frequency of approximately 30 breaths per minute for approximately 20 seconds. While the subject is breathing into sample bag 22, suction pump 32 is drawing the breath sample through conduit 34 to the sample collection chamber in the analyzer 36. When the subject is finished providing the breath sample, the operator presses the "continue" key 110 which terminates electrical current to all components. The operator then removes the mouthpiece 24 and the sample bag 22 and discards them. The operator again presses the "continue" key 110 which provides current to suction pump motor 78 for a preprogrammed length of time to purge conduit 34 of any remaining sample gases in preparation for sampling the next subject's breath.

It should be appreciated that the foregoing operational description is merely one manner of operating the isothermal rebreathing system involving the interaction of a human operator and subject, electrical and mechanical components, and computer software. Depending upon the sophistication desired and number of data sampling components included, the microcomputer system may be programmed to reduce the involvement of the human operator to merely turning on the system and insuring subject compliance with the controller 26 prompts. On the other hand, the monitoring and control of the various aforementioned temperatures and pressures may be accomplished entirely by a human operator without the need for microcomputer control. Therefore, the above functional description merely constitutes one functional embodiment for operating the system of the present invention.

EXAMPLE IV

The procedures of Example I were followed except that the subjects' rebreathed into an isothermal rebreathing system comprising a sample bag, made from polytetrafluoroethylene contained within a first box made from Lucite, a registered trademark, which was enclosed by a second Lucite box, the air around the second box heated to a temperature of approximately 37° C. The subjects commenced rebreathing into the sample bag at a rate of 20 breaths per minute. The alcohol concentration of the several cycles of the subjects' exhaled breath was recorded as a function of time with time zero beginning upon initial rebreathing into the sample bag. Data which was obtained during the testing of one subject and representative of data obtained from the group of subjects is provided below:

| Time (sec) | Calculated Alcohol Concentration (gm %) | Time (sec) | Calculated Alcohol Concentration (gm %) | Time (sec) | Calculated Alcohol Concentration (gm %) |
|---|---|---|---|---|---|
| 0 | 0 | 12 | .101 | 24 | .106 |
| 1 | .013 | 13 | .101 | 25 | .106 |
| 2 | .053 | 14 | .102 | 26 | .107 |
| 3 | .069 | 15 | .103 | 27 | .107 |
| 4 | .068 | 16 | .104 | 28 | .107 |
| 5 | .071 | 17 | .105 | 29 | .106 |
| 6 | .084 | 18 | .105 | 30 | .107 |
| 7 | .090 | 19 | .104 | 31 | .107 |
| 8 | .090 | 20 | .104 | 32 | .107 |
| 9 | .092 | 21 | .105 | 33 | .106 |
| 10 | .097 | 22 | .106 | 34 | .107 |
| 11 | .100 | 23 | .106 | 35 | .107 |

The representative blood alcohol concentration as determined from chemical analysis of the subjects' blood was 0.104 gm %.

What is claimed is:

1. An isothermal rebreathing apparatus for collecting breath gases from a subject, for analysis of selected chemical components comprising, in combination:
   a. an enclosed, sample bag having a maximum expanded volume which is at least as great as the subject's output volume;
   b. means for permitting a subject to rebreathe breath gases by repetitively exhaling the breath gases into and then inhaling the exhaled breath gases from said sample bag, said means including an inlet connected with said sample bag for allowing passage of the breath gases;
   c. means for maintaining the temperature of breath gases in the sample bag in substantial equilibrium with the subject's body temperature, including means for sensing the temperature of the breath gases in said sample bag; and
   d. means for extracting a sample of the breath gases from said bag when the sensed temperature of the breath gases are in substantial equilibrium with the subject's body temperature.

2. An isothermal rebreathing apparatus as set forth in claim 1 further comprising an enclosed heating container, said sample bag is positioned within said container, said means for permitting a subject to repetitively exhale into and inhale from said sample bag further including a mouthpiece connected with said sample bag within said heating container.

3. An isothermal rebreathing apparatus as set forth in claim 1 wherein said maintaining means further include means for measuring the subject's actual body temperature and for utilizing said said actual measured body temperature to establish a reference temperature, means for heating the breath gases within the container during the subject's rebreathing, and control means, responsive to the reference temperature and to the sensed temperature, for controlling said heating means.

4. An isothermal rebreathing apparatus as set forth in claims 1 or 2 wherein said means for extracting breath gases from said sample bag includes an evacuation conduit to connected with said sample bag and means for lowering the pressure within said evacuation conduit to about 200 mm Hg.

5. An isothermal rebreathing apparatus as set forth in claim 4 wherein said means for lowering the pressure within said evacuation conduit comprises a vacuum pump.

6. An isothermal rebreathing apparatus as set forth in claim 2 wherein said heating container includes a first chamber for enclosing said sample bag, a second chamber, and conduit means interconnecting said first and second chamber for permitting fluid communication therebetween as the volume of breath gases contained within said sample bag is increased and decreased as the subject exhales into and inhales from said sample bag.

7. An ieothermal rebreathing apparatus asset forth in claim 6 further including means for measuring a pressure drop across said conduit to determine a tidal volume of breath exhaled by the subject.

8. An isothermal rebreathing apparatus as set forth in claim 3 wherein said heating means comprises at least one incandescent lamp.

9. An isothermal rebreathing apparatus as set forth in claim 2 wherein said mouthpiece and and said sample bag are connected by a conduit having an internal diameter of one inch to minimize internal system resistance to breath exhalations emanating from subjects experiencing breathing impediments.

10. An isothermal rebreathing apparatus as set forth in claim 2 additionally comprising means, disposed within said mouthpiece for preheating the breath gases.

11. An isothermal rebreathing apparatus as set forth in claim 10 wherein said breath preheating means includes a plurality of electrical resistance heating elements formed in a honeycomb pattern, the plane thereof perpendicular to the direction of flow of the breath gases.

12. An isothermal rebreathing apparatus as set forth in claim 1 additionally comprising means for directing the subject to inhale and exhale breath gases at a predetermined frequency.

13. A method of collecting breath gases from a human subject for analysis of a chemical composition of the breath gases, comprising the steps of:
   a. causing the subject to rebreathe the breath gases by repetitively exhaling the breath gases into and then inhaling the exhaled breath gases from a sample bag;
   b. sensing the temperature of the breath gases in the sample bag during the subject's exhaling and inhaling;
   c. selecting a reference temperature which is substantially equal to the subject's body temperature;
   d. controlling the temperature of the breath gases in the sample bag so that the breath gases are brought into substantial equilibrium with the reference temperature;
   e. extracting the rebreathed gases exhaled into the sample bag by the subject after the temperature sensed within the sample bag has been brought into substantial equilibrium with the subject's body temperature; and
   f. analyzing the extracted length gases.

14. The method as set forth in claim 13 wherein the reference temperature is selected by measuring the actual temperature of the subject's body.

15. The method as set forth in claim 13 wherein the controlling step includes the step of heating the breath gases in the sample container to a temperature in substantial equilibrium with the subject's body temperature.

16. The method as set forth in claim 13 wherein during the causing step the subject is caused to inhale and exhale through a mouthpiece connected with the sample container; and wherein the mouthpiece is preheated to further maintain the breath gases in the mouthpiece in substantial thermal equilibrium with the selected reference temperature.

17. The method as set forth in claim 13 wherein the rebreathed gases are extracted from the sample bag by applying a reduced pressure thereto.

18. The method as set forth in claim 17 wherein the pressure is reduced to about 200 mm Hg.

19. The method as set forth in claim 13 wherein a tidal volume of the breath gases exhaled into the sample bag by the subject is further measured to ensure that the rebreathed gases exhaled by the subject contain a sample of alveolar gas originating in a deep region of the subject's lungs.

20. A method of collecting a breath sample from a human subject for analysis of the chemical content of the breath sample, comprising the steps of:
   a. causing the subject to repetitively rebreathe breath gases by exhaling the breath gases into and inhaling the exhaled breath gases from a sample container;
   b. sensing the temperature of the breath gases in the sample container during the subject's exhaling and inhaling, and generating a first output of the sensed breath gas temperature;
   c. selecting a reference temperature which is representative of the subject's normal body temperature and generating a second output of the selected body temperature;
   d. maintaining, in response to the first and second outputs, the breath gases in the sample container during the rebreathing at a temperature which is in substantial equilibrium with the selected reference temperature; and
   e. continuing to repetitively exhale the breath gases into and exhale the breath gases from the enclosed sample container to establish an equilibrium between the temperature of the subject's breath gases and the selected reference temperature.

21. An apparauts for obtaining breath gases from a subject for analysis of selected chemical components of the breath gases, comprising:
   a. means for collecting the breath gases, said collecting means including (i) a sample container, and (ii) an inlet connected to said sample container, said collecting means being engaged by the subject to repetitively rebreathe the breath gases through said inlet, said sample container having a maximum expanded volume which is at least as great as the output volume of the subject's breath gases; and
   b. means for maintaining the temperature of the breath gases in the sample container in substantial equilibrium with a selected reference temperature.

* * * * *